(12) United States Patent
Govari

(10) Patent No.: US 8,141,558 B2
(45) Date of Patent: Mar. 27, 2012

(54) POSITION DEPENDENT INTERFERENCE CANCELLATION

(75) Inventor: Assaf Govari, Haifa (IL)

(73) Assignee: Biosense Webster (Israel), Ltd. (IL)

( * ) Notice: Subject to any disclaimer, the term of this patent is extended or adjusted under 35 U.S.C. 154(b) by 7 days.

(21) Appl. No.: 12/816,505

(22) Filed: Jun. 16, 2010

(65) Prior Publication Data
US 2011/0308536 A1    Dec. 22, 2011

(51) Int. Cl.
*A61B 19/00* (2006.01)
(52) U.S. Cl. ........................................ 128/899
(58) Field of Classification Search .................. 600/407, 600/424, 300; 341/50, 65, 78; 128/897–899
See application file for complete search history.

(56) References Cited

U.S. PATENT DOCUMENTS

| | | | |
|---|---|---|---|
| 5,391,199 A | 2/1995 | Ben-Haim | |
| 6,147,480 A | 11/2000 | Osadchy | |
| 6,239,724 B1 | 5/2001 | Doron et al. | |
| 6,266,551 B1 * | 7/2001 | Osadchy et al. | 600/424 |
| 6,332,089 B1 | 12/2001 | Acker et al. | |
| 6,370,411 B1 * | 4/2002 | Osadchy et al. | 600/372 |
| 6,484,118 B1 | 11/2002 | Govari | |
| 6,618,612 B1 | 9/2003 | Acker et al. | |
| 6,690,963 B2 | 2/2004 | Ben-Haim et al. | |
| 7,860,553 B2 * | 12/2010 | Govari et al. | 600/424 |
| 2002/0065455 A1 | 5/2002 | Ben-Haim et al. | |
| 2003/0120150 A1 | 6/2003 | Govari | |
| 2004/0068178 A1 | 4/2004 | Govari | |
| 2006/0074289 A1 | 4/2006 | Adler et al. | |

FOREIGN PATENT DOCUMENTS

| | | |
|---|---|---|
| EP | 2 143 377 A1 | 1/2010 |
| WO | WO 96/05768 | 2/1996 |
| WO | WO 97/29678 A2 | 8/1997 |

OTHER PUBLICATIONS

EP Search Report No. EP 11 16 9932 Dated Sep. 9, 2011.

* cited by examiner

*Primary Examiner* — Samuel Gilbert
(74) *Attorney, Agent, or Firm* — Louis J. Capezzuto

(57) ABSTRACT

A method for position tracking includes receiving signals from a main position transducer at a distal end of a medical probe via wiring traversing the probe to a connector at a proximal end of the probe, for connection to a processor, which processes the signals to find a first position of the distal end. Calibration data with respect to an interference introduced into the signals at the connector is collected as a function of a position of the proximal end. A second position of an auxiliary position transducer at the proximal end of the probe is measured. The interference in the signals is canceled responsively to the measured second position and the calibration data. The first position is calculated based on the signals, after canceling the interference.

17 Claims, 3 Drawing Sheets

POSITION DEPENDENT INTERFERENCE CANCELLATION

FIELD OF THE INVENTION

The present invention relates generally to invasive probes, and specifically to determining the position of a medical probe inside a body cavity.

BACKGROUND

A wide range of medical procedures involve placing objects, such as sensors, tubes, catheters, dispensing devices and implants, within the body. Position sensing systems have been developed for tracking such objects. Magnetic position sensing is one of the methods known in the art. In magnetic position sensing, magnetic field generators are typically placed at known positions external to the patient. One or more magnetic field sensors within the distal end of a probe generate electrical signals in response to these magnetic fields, which are processed in order to determine the position coordinates of the distal end of the probe. These methods and systems are described in U.S. Pat. Nos. 5,391,199, 6,690,963, 6,484,118, 6,239,724, 6,618,612 and 6,332,089, in PCT International Publication WO 1996/005768, and in U.S. Patent Application Publications 2002/0065455 A1, 2003/0120150 A1 and 2004/0068178 A1, whose disclosures are all incorporated herein by reference.

U.S. Pat. No. 6,370,411, whose disclosure is incorporated herein by reference, describes a probe having two parts: a catheter of minimal complexity which is inserted into a patient's body, and a connection cable that connects between the proximal end of the catheter and the console. The catheter comprises a microcircuit that carries substantially only information specific to the catheter, which is not in common with other catheters of the same model. The cable comprises an access circuit which receives the information from the catheter and passes it in a suitable form to the console. In some embodiments, the cable operates with all catheters of a specific model or type, and therefore when a catheter is replaced, there is no need to replace the cable. Catheters that are planned for one-time use do not require replacement of the cable, which does not come in contact with patients.

U.S. Patent Application Publication 2006/0074289 A1, whose disclosure is incorporated herein by reference, discusses an endoscopic probe, whose handle has an orientation sensor that generates signals indicative of the orientation of the handle in an external frame of reference. The output of the orientation sensor may be used to sense movement of the handle relative to its initial position and orientation at the beginning of the endoscopic procedure.

SUMMARY OF THE INVENTION

An embodiment of the present invention that is described herein provides a method for position tracking, including:

receiving signals from a main position transducer at a distal end of a medical probe via wiring traversing the probe to a connector at a proximal end of the probe, for connection to a processor, which processes the signals to find a first position of the distal end;

collecting calibration data with respect to an interference introduced into the signals at the connector as a function of a position of the proximal end;

measuring a second position of an auxiliary position transducer at the proximal end of the probe;

canceling the interference in the signals responsively to the measured second position and the calibration data; and calculating the first position based on the signals, after canceling the interference.

In some embodiments, the medical probe includes a catheter. In an embodiment, the signals are generated by the main position transducer in response to one or more magnetic fields that are applied in a vicinity of the probe and sensed by the main position transducer. In another embodiment, the auxiliary position transducer is fitted adjacent to the connector. The auxiliary position transducer and the connector may be coupled to a handle of the probe. In another embodiment, collecting the calibration data includes placing the proximal end at a plurality of positions relative to a source of the interference, collecting auxiliary position signals from the auxiliary position transducer indicative of the respective positions of the proximal end, and measuring the interference as a function of the auxiliary position signals.

In yet another embodiment, measuring the second position includes applying one or more magnetic fields in a vicinity of the proximal end, receiving from the auxiliary position transducer signals that are generated by the auxiliary position transducer responsively to the magnetic fields, and calculating the second position based on the received signals. In still another embodiment, the method includes presenting the calculated first position to an operator.

There is additionally provided, in accordance with an embodiment of the present invention, apparatus, including:

a medical probe, which includes a distal end including a main position transducer, a proximal end including an auxiliary position transducer, a connector connecting the distal end to the proximal end, and wiring traversing the probe and coupling the main position transducer to the connector; and a processor, which is configured to receive from the main position transducer over the wiring signals, which are indicative of a first position of the distal end, to collect calibration data with respect to an interference introduced into the signals at the connector as a function of a position of the proximal end, to measure a second position of the auxiliary position transducer, to cancel the interference in the signals responsively to the measured second position and the calibration data, and to calculate the first position based on the signals, after canceling the interference.

There is also provided, in accordance with an embodiment of the present invention, a computer software product, operated in conjunction with a medical probe that includes a distal end including a main position transducer, a proximal end including an auxiliary position transducer, a connector connecting the distal end to the proximal end, and wiring traversing the probe and coupling the main position transducer to the connector, the product including a non-transitory computer-readable medium, in which program instructions are stored, which instructions, when read by a computer, cause the computer to receive from the main position transducer over the wiring signals, which are indicative of a first position of the distal end, to collect calibration data with respect to an interference introduced into the signals at the connector as a function of a position of the proximal end, to measure a second position of the auxiliary position transducer, to cancel the interference in the signals responsively to the measured second position and the calibration data, and to calculate the first position based on the signals, after canceling the interference.

The present invention will be more fully understood from the following detailed description of the embodiments thereof, taken together with the drawings in which:

DETAILED DESCRIPTION OF EMBODIMENTS

Overview

Figure 1:
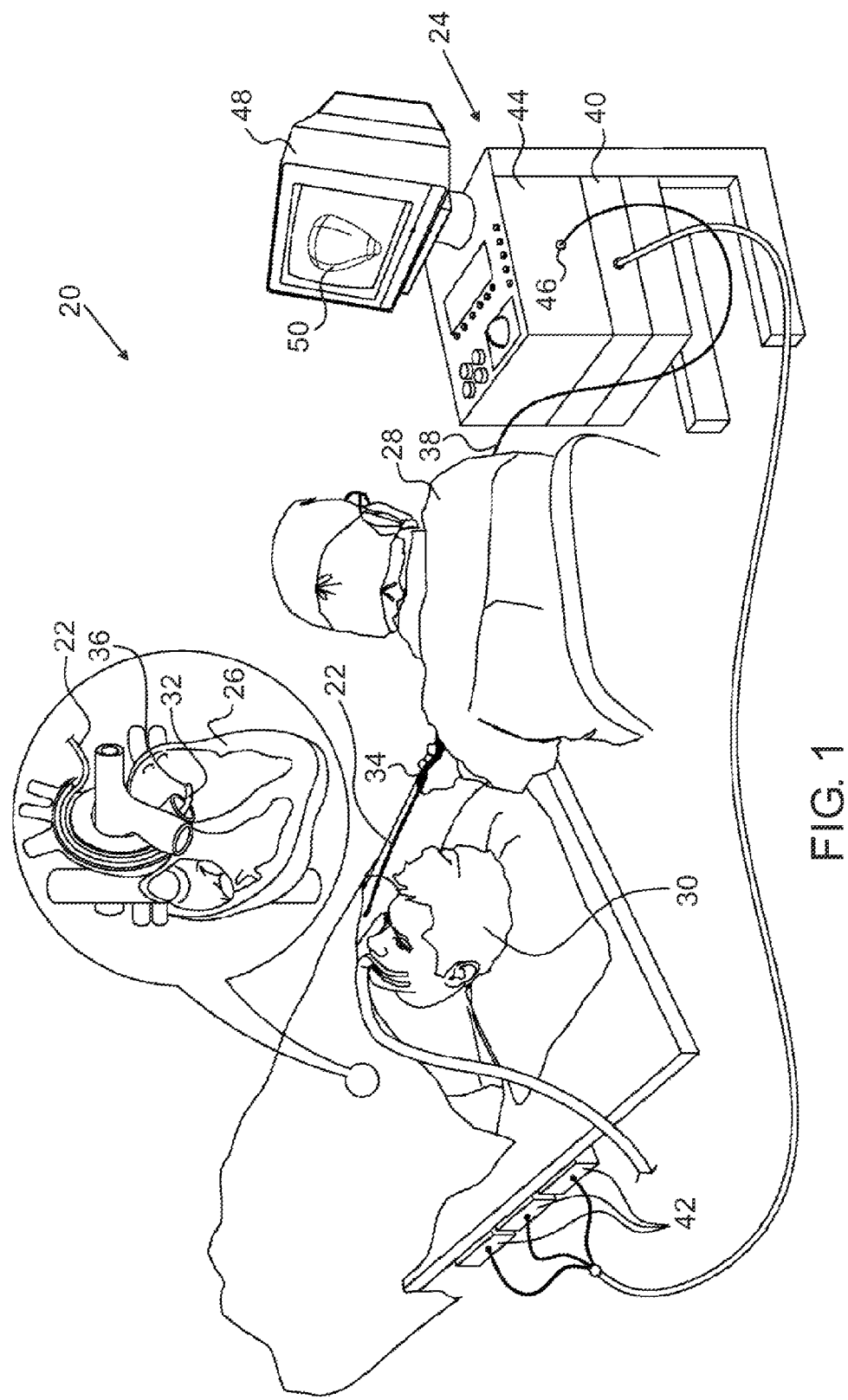
FIGS. 1 and 2 are schematic, pictorial illustrations of a medical position tracking system that uses interference cancellation, in accordance with an embodiment of the present invention.

Various diagnostic and therapeutic procedures, such as intracardiac electrical mapping and cardiac ablation, use an invasive probe that is inserted into a patient's body. In these procedures, it is sometimes important to ascertain the location of the probe within a body cavity. The location can be determined by a console which processes signals from a position transducer fitted in the distal tip.

Probe assemblies are sometimes implemented with a disposable distal part (e.g., the part of the catheter to be inserted in the body cavity) and a reusable proximal part (e.g., a cable carrying signals from the distal part to a processing console). The distal and proximal parts of the probe are typically connected to one another using a connector. The connector may be fitted, for example, in a handle of the probe. In this "split handle" configuration, wires conveying the signals from the position transducer in the distal tip to the console may be shielded against interference pickup, e.g., using shielded and/or twisted pair wiring. In the vicinity of the connector, however, continuous shielding may be difficult to achieve, because the wiring may need to be unwound in order to connect to the connector pins.

In some position tracking systems, the position transducer in the distal tip generates signals in response to a magnetic field that is generated by external field generators. In many practical implementations, the signals sent over the wiring in the probe are weak in comparison with the external magnetic field. As a result, the wiring may pick up interference from the external magnetic field, and this interference may distort the position measurements of the system. Since, as noted above, shielding may be degraded in the vicinity of the connector, interference pickup in that area may be particularly severe.

Embodiments of the present invention provide methods and systems for canceling interference that is picked-up in the vicinity of the connector. In some embodiments, an additional auxiliary position transducer is fitted in the handle, in close proximity to the connector. The signals produced by the auxiliary position transducer are indicative of the location and orientation of the handle (and thus of the connector). In a preparatory calibration procedure, the interference is measured as a function of the handle position, according to the signals produced by the auxiliary position transducer.

During an actual medical procedure, the console receives position measurements from the position transducer the distal tip (referred to as a main position transducer), as well as from the auxiliary position transducer in the handle. The console determines the position of the distal tip by canceling out the interference in the signals received from the main position transducer using the calibration data, based on the signals received from the auxiliary position transducer in the handle. Thus, the position of the distal tip can be measured with high accuracy, even in the presence of strong interference.

System Description

FIG. 1 is an illustration of a medical position tracking system 20 that uses interference cancellation, in accordance with an embodiment of the invention. System 20 may be based, for example, in the CARTO™ system, produced by Biosense Webster Inc. (Diamond Bar, Calif.). System 20 comprises a medical probe 22, such as a catheter, and a control console 24. In the embodiment described hereinbelow, it is assumed that probe 22 is used for diagnostic or therapeutic treatment, such as mapping electrical potentials in a heart 26 or performing ablation of heart tissue. Alternatively, probe 22 may be used, mutatis mutandis, for other therapeutic and/or diagnostic purposes in the heart or in other body organs.

An operator 28, such as a cardiologist, inserts probe 22 through the vascular system of a patient 30 so that a distal end 32 of probe 22 enters a chamber of the patient's heart 26. Holding probe 22 at a handle 34, operator 28 advances the probe, positioning a distal tip 36 at a desired location. Handle 34 couples probe 22 to a cable 38, which connects to console 24 via a suitable connector. The configuration of probe 22, and particularly handle 34, is shown in greater detail in FIG. 2 below.

Figure 2:
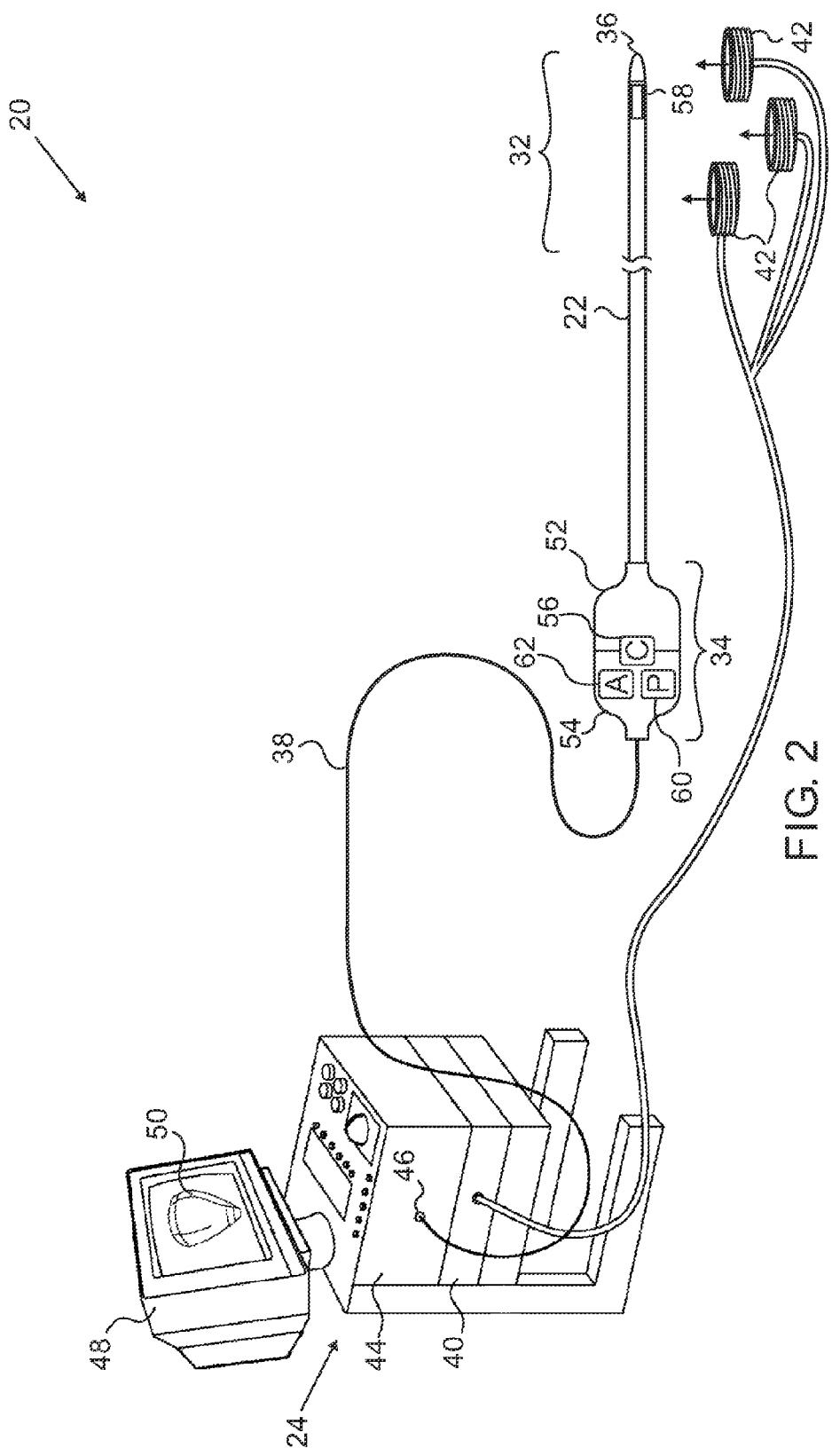

Console 24 uses magnetic position sensing to determine position coordinates of distal tip 36 inside heart 26. To determine the position coordinates, a driver circuit 40 in console 24 drives field generators 42 to generate magnetic fields within the body of patient 30. Typically, field generators 42 comprise coils, which are placed below the patient's torso at known positions external to patient 30. These coils generate magnetic fields in a predefined working volume that contains heart 26. Magnetic field transducers that are coupled to distal tip 36 and handle 34 generate electrical signals in response to these magnetic fields. A signal processor 44 in console 24 processes the electrical signals in order to determine the position coordinates of distal tip 36 and handle 34, typically including both location and orientation coordinates. As discussed supra, processor 44 can cancel out the interference in the signals received from a main position transducer in distal tip 36, based on the signals received from an auxiliary position transducer in handle 34. Both position transducers are shown in FIG. 2 below.

Processor 44 typically comprises a general-purpose computer, with suitable front end and interface circuits for receiving signals from probe 22 and controlling the other components of console 24. Processor 44 may be programmed in software to carry out the functions that are described herein. The software may be downloaded to console 24 in electronic form, over a network, for example, or it may be provided on non-transitory tangible media, such as optical, magnetic or electronic memory media. Alternatively, some or all of the functions of processor 44 may be carried out by dedicated or programmable digital hardware components, or using a combination of hardware and software elements.

An input/output (I/O) interface 46 enables console 24 to interact with probe 22. Based on the signals received from probe 22 (via interface 46 and other components of system 20), processor 44 drives a display 48 to present operator 28 with an image 50 showing the position of distal tip 36 in the patient's body, as well as status information and guidance regarding the procedure that is in progress.

Alternatively or additionally, system 20 may comprise an automated mechanism (not shown) for maneuvering and operating probe 22 within the body of patient 30. Such mechanisms are typically capable of controlling both the longitudinal motion (advance/retract) of probe 22 and transverse motion (deflection/steering) of distal end 32. In such embodiments, processor 44 generates a control input for controlling the motion of probe 22 based on the signals provided by the magnetic field transducers in the probe and the handle, as explained further hereinbelow.

FIG. 2 is another schematic, pictorial illustration of system 20, in accordance with an embodiment of the present invention. FIG. 2 shows the configuration of probe 22, and in particular handle 34, in greater detail. As can be seen in the figure, handle 34 connects probe 22 to cable 38, and comprises a distal part 52 and a proximal part 54 that mate via a suitable connector 56. Proximal part 54 of the handle and cable 38 are sometimes referred to as the proximal part of the probe. Distal part 56 of the handle, and catheter 22, are sometimes referred to as the distal part of the probe.

Distal tip 36 comprises a main position transducer 58, which generates a signal to console 24 that is indicative of the position coordinates of the distal tip relative to field generators 42. An auxiliary position transducer 60 is fitted in proximal part 54 of handle 34, and generates a signal to console 24 that is indicative of the position coordinates of the handle relative to field generators 42. Each of position transducers 58 and 60 may comprise one or more miniature coils, and typically comprise multiple coils oriented along different axes. Alternatively, position transducers 58 and 60 may comprise either another type of magnetic transducer, an electrode which serves as a position transducer, or position transducers of other types, such as impedance-based or ultrasonic position transducers. Although FIG. 2 shows a probe with a single position transducer in distal tip 36, embodiments of the present invention may utilize probes with more than one position transducer in the distal tip and/or distal end 32. When distal tip 36 is positioned in heart 26 during a medical procedure, processor 44 uses the signals received from position transducers 58 and 60 to calculate the position of the distal tip.

As discussed supra, position transducers 58 and 60 may generate weak signals due to their configuration. An amplifier 62 coupled to proximal part 54 amplifies the signals received from position transducers 58 and 60. The "split handle" configuration shown in FIG. 2 permits components such as amplifier 62 and auxiliary position transducer 60 to be contained in proximal part 54, which is reusable, while probe 22 is disposed of after use. Further aspects of split-handle configurations are addressed in U.S. Pat. No. 6,370,411, cited above.

In an alternative embodiment, the roles of position transducers 58, 60 and magnetic field generators 42 may be reversed. In other words, driver circuit 40 may drive magnetic field generators in position transducers 58 and 60, so as to generate magnetic fields. Coils 42 may be configured to sense the fields and generate signals indicative of the amplitudes of the components of these magnetic fields. In this embodiment, processor 44 receives and processes the signals from coils 42 in order to determine the position coordinates of distal tip 36 within heart 26.

Although FIGS. 1 and 2 show a particular system configuration, other system configurations can also be employed to implement embodiments of the present invention, and are thus considered to be within the spirit and scope of this invention. For example, the methods described hereinbelow may be applied using position transducers of other types, such as impedance-based or ultrasonic position transducers. The term "position transducer" as used herein refers to an element mounted on probe 22 or handle 34 which causes console 24 to receive signals indicative of the coordinates of the respective element. The position transducer may thus comprise a receiver on the probe or the handle, which generates a position signal to the control unit based on energy received by the transducer; or it may comprise a transmitter, emitting energy that is sensed by a receiver external to the probe or the handle. Furthermore, the methods described hereinbelow may similarly be applied in mapping and measurement applications using not only catheters, but also probes of other types, both in the heart and in other body organs and regions.

Position Measurement Using Interference Cancellation

Cable 38 conveys signals from main position transducer 58 to console 24 via handle 34. As discussed hereinabove, cable 38 may pick up interference that may distort the signals of the main position transducer. As a result, console 24 may err is calculating the position of distal tip 36. The interference picked-up by cable 38 may be caused by the relatively strong magnetic fields generated by generators 42, by various electrical signals in the vicinity of the probe, or by any other source.

Cable 38 typically comprises shielded, twisted-pair wires in order to avoid such undesired interference pickup. In the vicinity of connector 56, however, the shielding performance may be degraded because of the interconnection to the connector pins. Thus, some residual interference is sometimes picked-up in the vicinity of the connector.

System 20 reduces the effect of interference pickup in connector 56 by pre-calibrating and canceling this interference using auxiliary position transducer 60. In some embodiments, processor 44 first measures the interference pickup as a function of the position (location and orientation) of handle 34 relative to the source of the interference. Processor 44 then uses this calibration data for canceling the interference in the signals received from main position transducer 58 during an actual medical procedure. The position of distal tip 36 can thus be calculated with high accuracy, even in the presence of strong interference. Moreover, the disclosed techniques may permit relaxing of the shielding requirements of cable 38.

Figure 3:
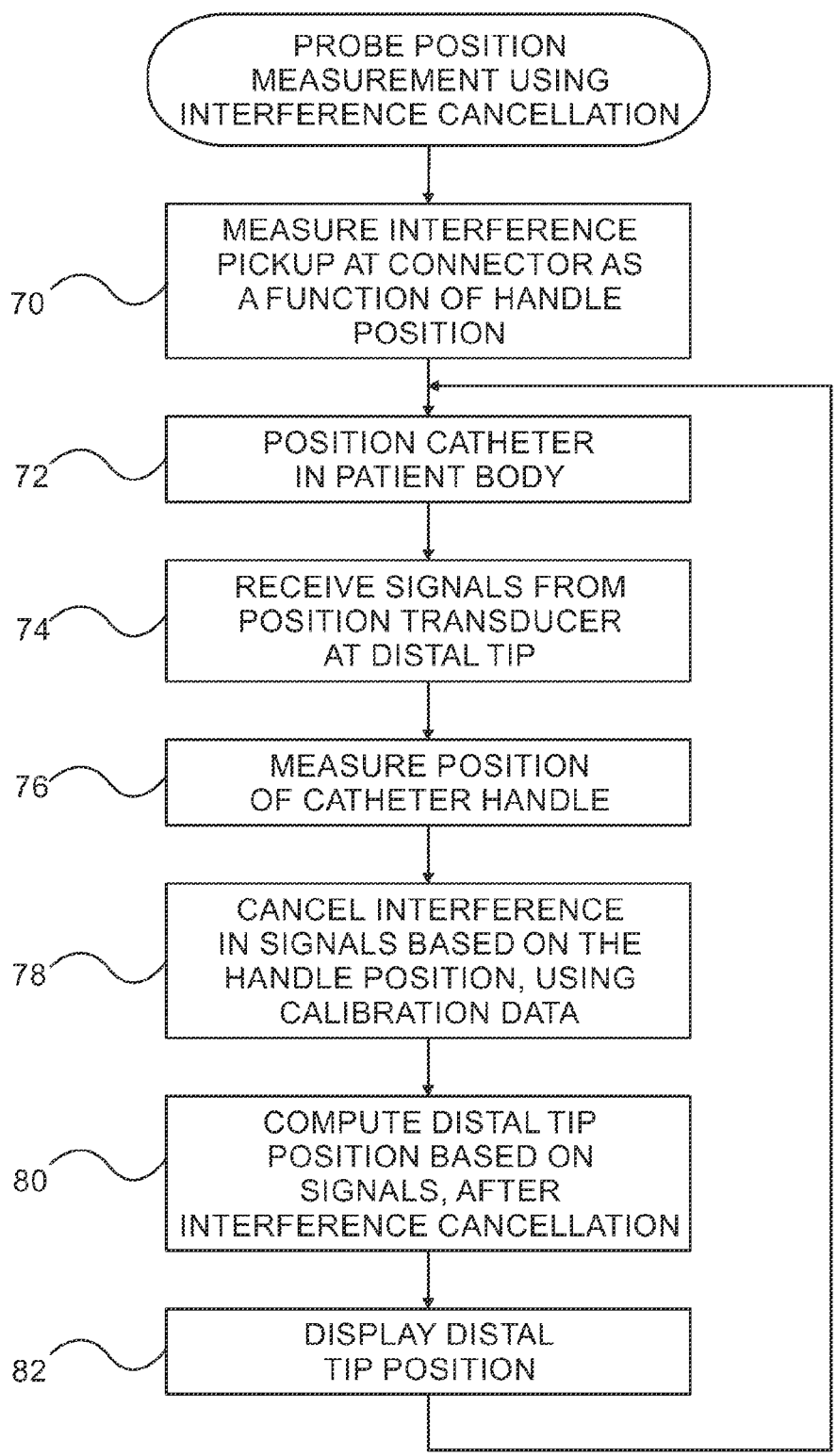
FIG. 3 is a flow diagram that schematically illustrates a method of measuring the position of a catheter using interference cancellation, in accordance with an embodiment of the present invention.

FIG. 3 is a flow diagram that schematically illustrates a method of measuring the position of distal tip 36 of probe using interference cancellation, in accordance with an embodiment of the present invention. At a preliminary calibration step 70, operator 28 positions handle 34 in multiple positions (locations and orientations) relative to field generators 42 (or other interference source). At each handle position, processor 44 measures the interference pickup at connector 56 as a function of the position of handle 34 (as measured by auxiliary position transducer 60). Processor 44 thus calibrates the interference amplitude as a function of the output of the auxiliary position transducer in the handle. The measured interference as a function of handle position is referred to as calibration data. Main position transducer 58 is typically disabled during the calibration procedure.

During a medical procedure, operator 28 manipulates handle 34 to position probe 22 in heart 26, at a probe positioning step 72. Processor 44 receives position signals from main position transducer 58 indicating the position of distal tip 36, at a main measurement step 74. Additionally, processor 44 receives position signals from auxiliary position transducer 60 indicating the position of handle 34, at an auxiliary measurement step 76.

Processor 44 cancels the interference in the signal received from main position transducer 58 based on the measured position of handle 34, at an interference cancellation step 78.

Typically, processor 44 queries the calibration data with the current position of the handle, as measured at step 76, so as to determine the expected interference level at this handle position. Processor 44 then subtracts the expected interference level from the signal of main position transducer 58, measured at step 74 above.

After canceling the interference, processor 44 computes the position of distal tip 36, at a tip positioning step 80. The calculation is performed using the position signal received from the main position transducer, after the interference has been canceled out from the signal. Finally, processor 44 presents image 50 on display 48, so as to display the location of distal tip 36 to operator 28, at an output step 82. The method returns to step 72 above.

Alternatively or additionally, the position measurements and interference cancellation scheme may be used in closed-loop control of an automated mechanism for maneuvering and operating probe 22, as described hereinabove, to ensure that the automated mechanism positions distal tip 36 in the proper location.

Although the embodiments described herein refer mainly to interference cancellation in medical position tracking systems, the disclosed techniques can be used for canceling position-dependent interference in various other applications.

The corresponding structures, materials, acts, and equivalents of all means or steps plus function elements in the claims below are intended to include any structure, material, or act for performing the function in combination with other claimed elements as specifically claimed. The description of the present disclosure has been presented for purposes of illustration and description, but is not intended to be exhaustive or limiting to the disclosure in the form disclosed. Many modifications and variations will be apparent to those of ordinary skill in the art without departing from the scope and spirit of the disclosure. The embodiment was chosen and described in order to best explain the principles of the disclosure and the practical application, and to enable others of ordinary skill in the art to understand the disclosure for various embodiments with various modifications as are suited to the particular use contemplated.

It is intended that the appended claims cover all such features and advantages of the disclosure that fall within the spirit and scope of the present disclosure. As numerous modifications and changes will readily occur to those skilled in the art, it is intended that the disclosure not be limited to the limited number of embodiments described herein. Accordingly, it will be appreciated that all suitable variations, modifications and equivalents may be resorted to, falling within the spirit and scope of the present disclosure.

The invention claimed is:

1. A method for position tracking, comprising:
   receiving signals from a main position transducer at a distal end of a medical probe via wiring traversing the probe to a connector at a proximal end of the probe, for connection to a processor, which processes the signals to find a first position of the distal end;
   collecting calibration data with respect to an interference introduced into the signals at the connector as a function of a position of the proximal end;
   measuring a position of an auxiliary position transducer at the proximal end of the probe;
   canceling the interference in the signals responsively to the measured position of the auxiliary position transducer and the calibration data; and
   calculating the first position of the distal end based on the signals, after canceling the interference.

2. The method according to claim 1, wherein the medical probe comprises a catheter.

3. The method according to claim 1, wherein the signals are generated by the main position transducer in response to one or more magnetic fields that are applied in a vicinity of the probe and sensed by the main position transducer.

4. The method according to claim 1, wherein the auxiliary position transducer is fitted adjacent to the connector.

5. The method according to claim 4, wherein the auxiliary position transducer and the connector are coupled to a handle of the probe.

6. The method according to claim 4, wherein collecting the calibration data comprises placing the proximal end at a plurality of positions relative to a source of the interference, collecting auxiliary position signals from the auxiliary position transducer indicative of the respective positions of the proximal end, and measuring the interference as a function of the auxiliary position signals.

7. The method according to claim 1, wherein measuring the position of the auxiliary position transducer comprises applying one or more magnetic fields in a vicinity of the proximal end, receiving from the auxiliary position transducer signals that are generated by the auxiliary position transducer responsively to the magnetic fields, and calculating the position of the auxiliary position transducer based on the received signals.

8. The method according to claim 1, and comprising presenting the calculated first position of the distal end to an operator.

9. Apparatus, comprising:
   a medical probe, which comprises a distal end comprising a main position transducer, a proximal end comprising an auxiliary position transducer, a connector at the proximal end operatively connected to a processor, and wiring traversing the probe and coupling the main position transducer to the connector; and
   the processor, which is configured to receive from the main position transducer over the wiring signals, which are indicative of a first position of the distal end, to collect calibration data with respect to an interference introduced into the signals at the connector as a function of a position of the proximal end, to measure a position of the auxiliary position transducer, to cancel the interference in the signals responsively to the measured position of the auxiliary position transducer and the calibration data, and to calculate the first position of the distal end based on the signals, after canceling the interference.

10. The apparatus according to claim 9, wherein the medical probe comprises a catheter.

11. The apparatus according to claim 9, wherein the signals are generated by the main position transducer in response to one or more magnetic fields that are applied in a vicinity of the probe and sensed by the main position transducer.

12. The apparatus according to claim 9, wherein the auxiliary position transducer is fitted adjacent to the connector.

13. The apparatus according to claim 12, wherein the probe comprises a handle, and wherein the auxiliary position transducer and the connector are coupled to the handle.

14. The apparatus according to claim 12, wherein the processor is configured to collect the calibration data by collecting a plurality of auxiliary position signals from the auxiliary position transducer while the proximal end is placed at respective positions relative to a source of the interference, and measuring the interference as a function of the auxiliary position signals.

15. The apparatus according to claim 9, wherein the processor is configured to receive from the auxiliary position transducer signals, which are generated by the auxiliary position transducer responsively to one or more magnetic fields applied in a vicinity of the proximal end, and to calculate the position of the auxiliary position transducer based on the received signals.

16. The apparatus according to claim 9, wherein the processor is configured to present the calculated first position of the distal end to an operator.

17. A computer software product, operated in conjunction with a medical probe that includes a distal end comprising a main position transducer, a proximal end comprising an auxiliary position transducer, a connector connecting the distal end to the proximal end, and wiring traversing the probe and coupling the main position transducer to the connector, the product comprising a non-transitory computer-readable medium, in which program instructions are stored, which instructions, when read by a computer, cause the computer to receive from the main position transducer over the wiring signals, which are indicative of a first position of the distal end, to collect calibration data with respect to an interference introduced into the signals at the connector as a function of a position of the proximal end, to measure a position of the auxiliary position transducer, to cancel the interference in the signals responsively to the measured position of the auxiliary position transducer and the calibration data, and to calculate the first position of the distal end based on the signals, after canceling the interference.

* * * * *